US010765892B1

(12) United States Patent
Vitek et al.

(10) Patent No.: US 10,765,892 B1
(45) Date of Patent: Sep. 8, 2020

(54) SYSTEMS AND METHODS FOR OPTIMIZING TRANSCRANIAL ULTRASOUND FOCUSING

(71) Applicants: Shuki Vitek, Haifa (IL); Yoav Levy, Hinanit (IL)

(72) Inventors: Shuki Vitek, Haifa (IL); Yoav Levy, Hinanit (IL)

(73) Assignee: INSIGHTEC, LTD., Tirat Carmel (IL)

( * ) Notice: Subject to any disclaimer, the term of this patent is extended or adjusted under 35 U.S.C. 154(b) by 645 days.

(21) Appl. No.: 15/613,940

(22) Filed: Jun. 5, 2017

(51) Int. Cl.
*A61N 7/00* (2006.01)

(52) U.S. Cl.
CPC ........ *A61N 7/00* (2013.01); *A61N 2007/0021* (2013.01)

(58) Field of Classification Search
CPC .......................... A61N 7/00; A61N 2007/0021
See application file for complete search history.

(56) References Cited

U.S. PATENT DOCUMENTS

| 4,669,311 A * | 6/1987 | McKinnon ........... A61B 8/0825 73/598 |
| 2013/0338485 A1* | 12/2013 | Mougenot .............. A61B 8/406 600/411 |
| 2014/0018671 A1* | 1/2014 | Li ............................ A61B 6/12 600/424 |
| 2014/0200489 A1* | 7/2014 | Behar ...................... A61N 7/00 601/3 |
| 2015/0133826 A1* | 5/2015 | Viitala ..................... A61N 7/02 601/3 |
| 2015/0196280 A1* | 7/2015 | Yamamoto ........... A61B 8/5269 600/440 |
| 2015/0273245 A1* | 10/2015 | Nurmilaukas ........... A61N 7/02 601/3 |
| 2016/0184026 A1* | 6/2016 | Tlusty ................... A61B 6/501 600/411 |

* cited by examiner

*Primary Examiner* — Bo Joseph Peng
(74) *Attorney, Agent, or Firm* — Morgan, Lewis & Bockius LLP

(57) ABSTRACT

Systems and methods for predicting a phase correction of ultrasound waves transmitted from one or more transducer elements and traversing a patient's skull into a target region utilizing data of the patient's skull include predicting a first beam path of the ultrasound waves traversing the skull based at least in part on the target location; computationally determining structural characteristics of the skull along the first beam path based on the acquired imaging data; and predicting a second beam path of the ultrasound waves traversing the skull based at least in part on the determined structural characteristics, thereby accounting for refraction resulting from the skull.

46 Claims, 10 Drawing Sheets

SYSTEMS AND METHODS FOR OPTIMIZING TRANSCRANIAL ULTRASOUND FOCUSING

FIELD OF THE INVENTION

The present invention relates, generally, to therapeutic ultrasound focusing and, more particularly, to systems and methods for optimizing ultrasound focusing through a non-uniform tissue, such as the skull, at a target location.

BACKGROUND

Focused ultrasound (i.e., acoustic waves having a frequency greater than about 20 kiloHertz) can be used to image or therapeutically treat internal body tissues within a patient. For example, ultrasound waves may be used in applications involving ablation of tumors, thereby eliminating the need for invasive surgery, targeted drug delivery, control of the blood-brain barrier, lysing of clots, and other surgical procedures. During tumor ablation, a piezoceramic transducer is placed externally to the patient, but in close proximity to the tissue to be ablated (i.e., the target). The transducer converts an electronic drive signal into mechanical vibrations, resulting in the emission of acoustic waves. The transducer may be geometrically shaped and positioned along with other such transducers so that the ultrasound energy they emit collectively forms a focused beam at a "focal zone" corresponding to (or within) the target tissue region. Alternatively or additionally, a single transducer may be formed of a plurality of individually driven transducer elements whose phases can each be controlled independently. Such a "phased-array" transducer facilitates steering the focal zone to different locations by adjusting the relative phases among the transducers. As used herein, the term "element" means either an individual transducer in an array or an independently drivable portion of a single transducer. Magnetic resonance imaging (MRI) may be used to visualize the patient and target, and thereby to guide the ultrasound beam.

The noninvasive nature of ultrasound surgery is particularly appealing for the treatment of brain tissue. Moreover, coherent, non-invasive focusing of ultrasound through the human skull has been considered as a tool for targeted drug delivery to the brain, improved thrombolytic stroke treatment, blood flow imaging, the detection of internal bleeding, and tomographic brain imaging. However, the human skull has been a barrier to the clinical realization of many of these applications. Impediments to transcranial procedures include strong distortions caused by irregularities in the skull's shape, density, and thickness, which contribute toward destroying the ultrasound focus, displacing the focus from a desired target location, and/or decreasing the ability to spatially register received diagnostic information.

Accordingly, there is a need for an approach that predicts the effects on the ultrasound beam traversing the skull and based thereon optimizes ultrasound focusing at a desired target location.

SUMMARY

The present invention provides, in various embodiments, systems and methods for estimating, using an acoustic ray model, one or more beam paths of ultrasound waves transmitted from one or more transducer elements to a target location through the patient's skull; the estimated beam path is then compared against the location of the target to determine a deviation therebetween. If the deviation is above a predetermined threshold (e.g., where a clinically significant effect is observed), an updated beam path may be estimated based at least in part on the previously predicted beam path and the determined deviation. This adjustment process may be iteratively performed until the deviation of the estimated beam path from the desired target location is below the predetermined threshold and/or reaches a minimum. A treatment protocol (e.g., parameter(s) associated with the ultrasound beams) corresponding to the minimal deviation (or the deviation below the threshold) may be executed during a focused ultrasound procedure to treat the target region.

In addition, a focusing algorithm may be implemented to determine the phases (and, optionally, amplitudes) associated with the transducer elements based on the path between the elements and target region such that constructive interference (i.e., a focus) of the ultrasound waves from the transducer elements occurs at the target region.

Accordingly, embodiments of the present invention may effectively eliminate (or at least reduce) focus smearing and/or a locational deviation between the target region and the focus of ultrasound beams resulting from the skull; this may ensure accurate delivery of ultrasound energy to the target region for increased treatment efficacy as well as avoiding damage to healthy tissue surrounding the target region. While developed mostly for non-invasive brain surgery and imaging, the approach of the invention may also be applied to other parts of the body requiring the penetration of ultrasound through a bone or cartilage interface.

Accordingly, in one aspect, the invention pertains to a method of transmitting ultrasound waves from one or more transducer elements and traversing a patient's skull into a target region utilizing data of the patient's skull. In various embodiments, the method includes (a) predicting a first beam path of the ultrasound waves traversing the skull into the target region based at least in part on a location of the target region; (b) computationally determining structural characteristics of the skull along the first beam path based on the skull data; (c) predicting a second beam path of the ultrasound waves traversing the skull based at least in part on the determined structural characteristics; (d) updating the second beam path of the ultrasound waves based at least in part on at least one of a deviation between the second beam path and the location of the target region or the second beam path; and (e) activating the transducer element(s) in accordance with a treatment protocol. The treatment protocol may include an amplitude and/or a phase shift associated with the transducer element(s). In addition, the method may include activating the transducer element(s) based at least in part on the determined second beam path. In some embodiments, the method further includes step (f) computationally updating the structural characteristics of the skull based at least in part on the second beam path prior to performing step (d). In some embodiments, the method further includes activating multiple transducer elements in accordance with the treatment protocol so as to generate a focus at the target region. In addition, the method may include, prior to step (e), (f) computationally determining a second deviation between the updated second beam path and the location of the target region; (g) determining whether the second deviation is above a predetermined threshold and, if so, (h) updating the updated second beam path of the ultrasound waves based at least in part on the second deviation; steps (f)-(h) may be iteratively performed until a stopping condition is satisfied. The stopping condition may occur when (i) the second deviation is below the predetermined threshold, (ii) a number of iterations exceeds a predetermined limit, and/or a change in the second deviation between two iterations is below a predetermined minimum.

In one implementation, the first beam path is or comprises one or more straight lines connecting the transducer element(s) to the target region. In addition, the skull data may be CT imaging data and the structural characteristics may be represented by a CT value extracted from the CT imaging data. The ultrasound waves may be transmitted from multiple transducer elements. In one embodiment, the second beam path of the ultrasound waves is adjusted by altering relative phases of the ultrasound waves emitted from the transducer elements. The method may further include computing amplitudes and/or phase shifts associated with the transducer elements so as to generate a focus at the target region. The skull's multiple layers may be considered in generating the focus; additionally, step (b) may include computationally determining structural characteristics of the skull layers based on the skull data, and step (c) may include predicting the second beam path of the ultrasound waves based at least in part on the determined structural characteristics of the skull layers. In one implementation, soft tissue located between the transducer element(s) and the skull is modeled as one of the skull layers. Information about the soft tissue may be acquired using any suitable imaging modality (e.g., an MRI apparatus).

In various embodiments, the method further includes establishing a relationship between the structural characteristics of multiple skull regions and speeds of ultrasound waves traversing the skull regions. The method may include determining a first speed of ultrasound for waves traversing the skull based on, for example, the relationship and the structural characteristics determined in step (b). In addition, the method may include determining a second speed of ultrasound for waves traversing brain and a third speed of ultrasound for waves traversing a medium located between the transducer element(s) and the skull. The third speed of ultrasound waves may be determined based at least in part on the temperature of the medium. In one embodiment, the second beam path is predicted based at least in part on the first, second and third speeds of ultrasound waves.

In some embodiments, the deviation determination step includes computing the shortest distance between the second beam path and the location of the target. In addition, the method may further include computing one or more angles between the first line(s) connecting the transducer element(s) to the location of the target region and the second line(s) connecting the transducer element(s) to a point (e.g., a point having a shortest distance to the location of the target region) on the second beam path; and updating the second beam path of the ultrasound waves based on the computed angle(s).

In another aspect, the invention relates to a system for transmitting ultrasound waves traversing a patient's skull into a target region. In various embodiments, the system includes an ultrasound transducer having one or more transducer elements for transmitting ultrasound waves; and a controller, operably coupled to the ultrasound transducer and imaging system. The controller is configured to (a) acquire data of the patient's skull; (b) predict a first beam path of the ultrasound waves traversing the skull into the target region based at least in part on a location of the target region; (c) computationally determine structural characteristics of the skull along the first beam path based on the skull data; (d) predict a second beam path of the ultrasound waves traversing the skull based at least in part on the determined structural characteristics; (e) update the second beam path of the ultrasound based at least in part on at least one of a deviation between the second beam path and the location of the target region or the second beam path; and (f) activate the transducer element(s) in accordance with a treatment protocol. The treatment protocol may include an amplitude and/or a phase shift associated with the transducer element(s). In addition, the controller may be further configured to activate the transducer element(s) based at least in part on the determined second beam path. In some embodiments, the controller, prior to performing step (e), is further configured to computationally update the structural characteristics of the skull based at least in part on the second beam path. In some embodiments, the controller is further configured to activate multiple transducer elements in accordance with the treatment protocol so as to generate a focus at the target region. In addition, the controller, prior to performing step (f), may be further configured to (g) computationally determine a second deviation between the updated second beam path and the location of the target region; (h) determine whether the second deviation is above a predetermined threshold and, if so, (i) update the updated second beam path of the ultrasound waves based at least in part on the second deviation; the controlled may be configured to perform steps (g)-(i) iteratively until a stopping condition is satisfied. The stopping condition may occur when (i) the second deviation is below the predetermined threshold, (ii) a number of iterations exceeds a predetermined limit, and/or a change in the second deviation between two iterations is below a predetermined minimum.

In one implementation, the controller is configured to predict the first beam path using one or more straight lines connecting the transducer element(s) to the target region. In addition, the system may include an imaging system comprising a computer tomography device for acquiring the skull data; the structural characteristics are represented by a CT value extracted from the imaging data acquired using the computer tomography device. The ultrasound transducer may include multiple transducer elements. In one embodiment, the controller is further configured to update the second beam path of the ultrasound waves by altering relative phases of the ultrasound waves emitted from the transducer elements. In another embodiment, the controller is further configured to compute amplitudes and/or phase shifts associated with the transducer elements so as to generate a focus at the target region. In various embodiments, the skull includes multiple layers, and the controller is further configured to computationally determine structural characteristics of the skull layers based on the imaging data in step (c) and predict the second beam path of the ultrasound waves based at least in part on the determined structural characteristics of the skull layers in step (d). In one implementation, the controller is further configured to model soft tissue located between the transducer element(s) and the skull as one of the skull layers.

In various embodiments, the controller is further configured to establish a relationship between the structural characteristics of multiple skull regions and speeds of ultrasound waves traversing the skull regions. The controller may be further configured to determine a first speed of ultrasound waves traversing the skull based on, for example, the relationship and the structural characteristics determined in step (b). In addition, the controller may be further configured to determine a second speed of ultrasound waves traversing brain tissue inside the skull and a third speed of ultrasound waves traversing a medium located between the transducer element(s) and the skull. The controller may be further configured to determine the third speed of ultrasound waves based at least in part on the temperature of the medium. In one embodiment, the controller is further configured to predict the second beam path based at least in part on the first, second and third speeds of ultrasound waves.

In some embodiments, the controller is further configured to compute the shortest distance between the second beam path and the location of the target so as to determine the deviation. In addition, the controller may be further configured to compute one or more angles between the first line(s) connecting the transducer element(s) to the location of the target region and the second line(s) connecting the transducer element(s) to a point (e.g., a point having a shortest distance to the location of the target region) on the second beam path; and update the second beam path of the ultrasound waves based on the computed angle(s).

Another aspect of the invention relates to a method of predicting the phase correction of ultrasound waves transmitted from one or more transducer elements and traversing a patient's skull into a target region utilizing data of the patient's skull. In various embodiments, the method includes predicting a first beam path of the ultrasound waves traversing the skull into the target region based at least in part on a location of the target region; computationally determining structural characteristics of the skull along the first beam path based on the skull data; an predicting a second beam path of the ultrasound waves traversing the skull based at least in part on the determined structural characteristics, thereby accounting for refraction resulting from the skull.

In yet another aspect, the invention pertains to a system for predicting the phase correction of ultrasound waves traversing a patient's skull into a target region. In various embodiments, the system includes an ultrasound transducer having one or more transducer elements for transmitting the ultrasound waves and a controller operably coupled to the imaging system. The controller is configured to acquire data of the patient's skull; predict a first beam path of the ultrasound waves traversing the skull into the target region based at least in part on a location of the target region; computationally determine structural characteristics of the skull along the first beam path based on the skull data; and predict a second beam path of the ultrasound waves traversing the skull based at least in part on the determined structural characteristics, thereby accounting for refraction resulting from the skull.

As used herein, the terms "approximately" and "substantially" mean±10%, and in some embodiments, ±5%. "Clinically significant" means having an undesired (and sometimes the lack of a desired) effect on tissue that is considered significant by clinicians, e.g., the onset of damage thereto. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

The foregoing will be more readily understood from the following detailed description of the invention in conjunction with the drawings, wherein.

DETAILED DESCRIPTION

Figure 1A:
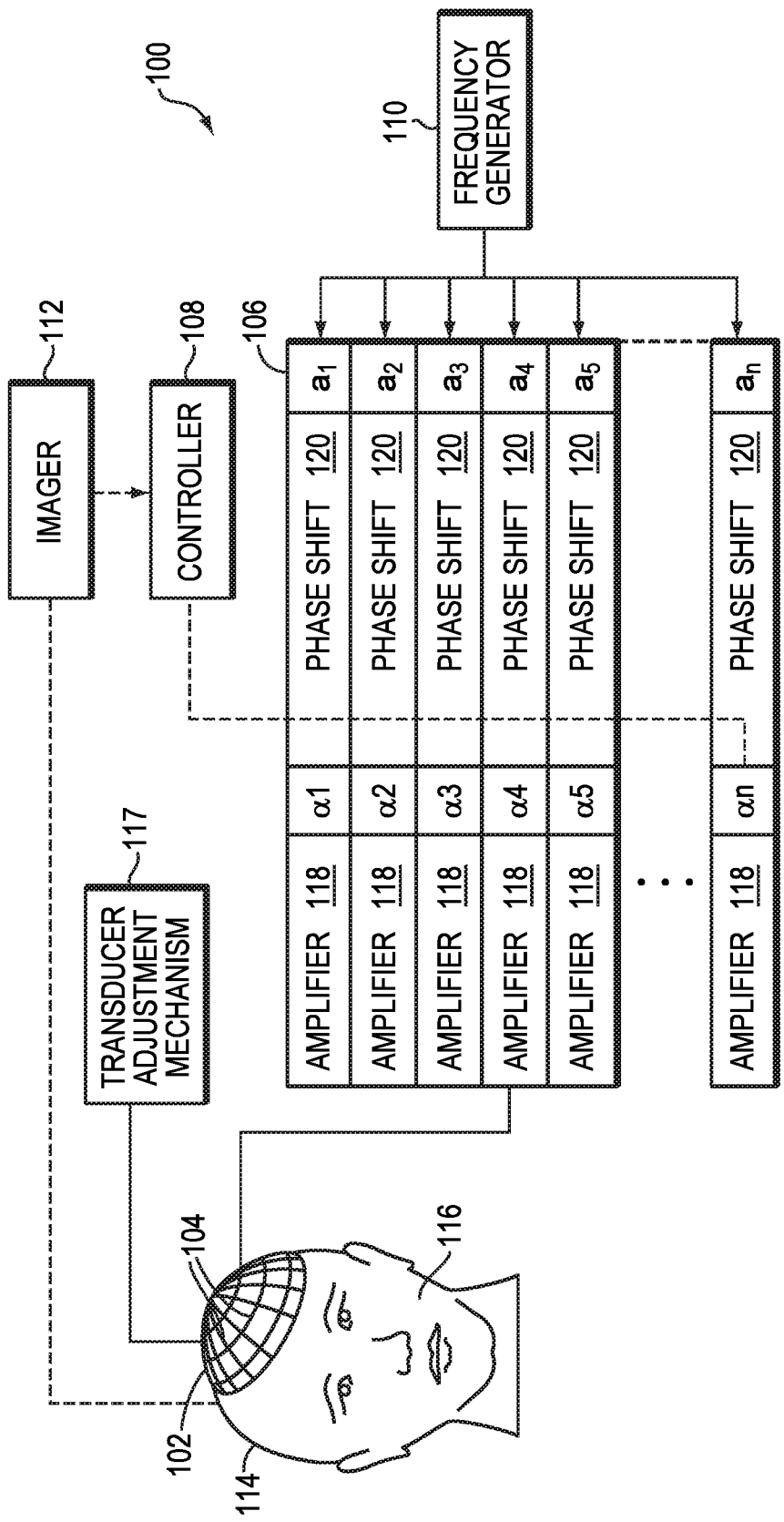
FIG. 1A schematically depicts an exemplary ultrasound system in accordance with various embodiments of the current invention.

FIG. 1A illustrates an exemplary ultrasound therapy system 100 for focusing ultrasound onto a patient's brain through the skull. The system 100 includes a phased array 102 of transducer elements 104, a beamformer 106 driving the phased array 102, a controller 108 in communication with the beamformer 106, and a frequency generator 110 providing an input electronic signal to the beamformer 106. In various embodiments, the system further includes an imager 112, such as a magnetic resonance imaging (MRI) device, a computer tomography (CT) device, a positron emission tomography (PET) device, a single-photon emission computed tomography (SPECT) device, or an ultrasonography device, for determining anatomical characteristics of the skull 114 of a patient 116.

The array 102 may have a curved (e.g., spherical or parabolic) shape suitable for placing it on the surface of the skull 114, or may include one or more planar or otherwise shaped sections. Its dimensions may vary, depending on the application, between millimeters and tens of centimeters. The transducer elements 104 of the array 102 may be piezoelectric ceramic elements, and may be mounted in silicone rubber or any other material suitable for damping the mechanical coupling between the elements 104. Piezo-composite materials, or generally any materials capable of converting electrical energy to acoustic energy, may also be used. To assure maximum power transfer to the transducer elements 104, the elements 104 may be configured for electrical resonance at 50Ω, matching input connector impedance. In addition, the system may include a transducer-adjustment mechanism 117 (e.g., a motor, a gimbal, or other manipulator that permits mechanical and/or electrical adjustment of the orientation (e.g., an angle or a position) and/or translation (if desired) of ultrasound beams emitted from the transducer array 102 and/or individual transducer elements 104 therein. For example, the transducer-adjustment mechanism 117 may physically rotate the transducer elements 104 around one or more axes thereof and/or move the elements 104 with respect to the skull 114 to a desired location. Alternatively or additionally, the transducer-adjustment mechanism 117 may adjust the orientation of the ultrasound beam electronically by changing the beam path via the beamformer 106, which responsively alters the relative phases of the transducer elements so as to change the beam path. In some embodiments, the transducer-adjustment mechanism 117 is responsive to a communication from the controller 108.

The transducer array 102 is coupled to the beamformer 106, which drives the individual transducer elements 104 so that they collectively produce a focused ultrasonic beam or field. For n transducer elements, the beamformer 106 may contain n driver circuits, each circuit including or consisting of an amplifier 118 and a phase delay circuit 120; drive circuit drives one of the transducer elements 104. The beamformer 106 receives a radio frequency (RF) input signal, typically in the range from 0.1 MHz to 1.0 MHz, from the frequency generator 110, which may, for example, be a Model DS345 generator available from Stanford Research Systems. The input signal may be split into n channels for the n amplifiers 118 and delay circuits 120 of the beamformer 106. In some embodiments, the frequency generator 110 is integrated with the beamformer 106. The radio frequency generator 110 and the beamformer 106 are configured to drive the individual transducer elements 104 of the transducer array 102 at the same frequency, but at different phases and/or different amplitudes.

The amplification or attenuation factors $\alpha_1$-$\alpha_n$ and the phase shifts $a_1$-$a_n$ imposed by the beamformer 106 serve to transmit and focus ultrasonic energy through the patient's skull 114 onto a selected region of the patient's brain, and account for wave distortions induced in the skull 114 and soft brain tissue. The amplification factors and phase shifts are computed using the controller 108, which may provide the computational functions through software, hardware, firmware, hardwiring, or any combination thereof. For example, the controller 108 may utilize a general-purpose or special-purpose digital data processor programmed with software in a conventional manner, and without undue experimentation, in order to determine the phase shifts and amplification factors necessary to obtain a desired focus at the target region. In certain embodiments, the computation is based on detailed information about the characteristics (e.g., structure, thickness, density, etc.) of the skull 114. Such information may be obtained from the imager 112. Image acquisition may be three-dimensional or, alternatively, the imager 112 may provide a set of two-dimensional images suitable for reconstructing a three-dimensional image of the skull 114 from which thicknesses and densities can be inferred. Image-manipulation functionality may be implemented in the imager 112, in the controller 108, or in a separate device.

System 100 may be modified in various ways within the scope of the invention. For example, for diagnostic applications, the system may further include a detector device (not shown) that measures transmitted or reflected ultrasound, and which may provide the signals it receives to the controller 108 for further processing. The reflection and transmission signals may also be used as feedback for the phase and amplitude adjustments of the beamformer 106. The system 100 may contain a mechanical positioner for arranging the array 102 of transducer elements 104 with respect to the patient's skull 114. In order to apply ultrasound therapy to body parts other than the brain, the transducer array 102 may take a different, e.g., a cylindrical, shape. In some embodiments, the transducer elements 104 are mounted movably and rotatably, providing mechanical degrees of freedom that can be exploited to improve focusing properties. Such movable transducers may be adjusted by conventional actuators, which may be driven by a component of controller 108 or by a separate mechanical controller.

Figure 1B:
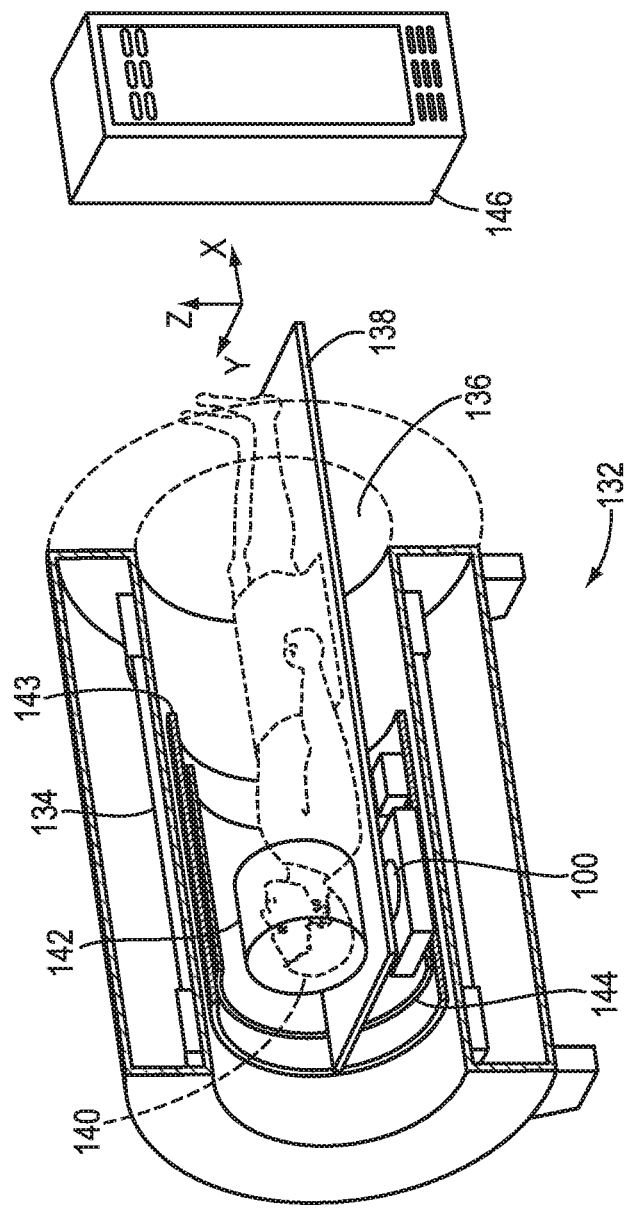
FIG. 1B schematically depicts an exemplary MRI system in accordance with various embodiments of the current invention.

In various embodiments, the imager 112 is an MRI apparatus. With reference to FIG. 1B, the MRI apparatus 132 may include a cylindrical electromagnet 134, which generates the requisite static magnetic field within a bore 136 of the electromagnet 134. During medical procedures, a patient is placed inside the bore 136 on a movable support table 138. A region of interest 140 within the patient (e.g., the patient's head) may be positioned within an imaging region 142 wherein the electromagnet 134 generates a substantially homogeneous field. A set of cylindrical magnetic field gradient coils 143 may also be provided within the bore 136 and surrounding the patient. The gradient coils 143 generate magnetic field gradients of predetermined magnitudes, at predetermined times, and in three mutually orthogonal directions. With the field gradients, different spatial locations can be associated with different precession frequencies, thereby giving an MR image its spatial resolution. An RF transmitter coil 144 surrounding the imaging region 142 emits RF pulses into the imaging region 142 to cause the patient's tissues to emit magnetic-resonance (MR) response signals. Raw MR response signals are sensed by the RF coil 144 and passed to an MR controller 146 that then computes an MR image, which may be displayed to the user. Alternatively, separate MR transmitter and receiver coils may be used. Images acquired using the MRI apparatus 132 may provide radiologists and physicians with a visual contrast between different tissues and detailed internal views of a patient's anatomy that cannot be visualized with conventional x-ray technology.

The MRI controller 146 may control the pulse sequence, i.e., the relative timing and strengths of the magnetic field gradients and the RF excitation pulses and response detection periods. The MR response signals are amplified, conditioned, and digitized into raw data using a conventional image-processing system, and further transformed into arrays of image data by methods known to those of ordinary skill in the art. Based on the image data, a treatment target region (e.g., a tumor in the brain) may be identified. The image-processing system may be part of the MRI controller 146, or may be a separate device (e.g., a general-purpose computer containing image-processing software) in communication with the MRI controller 146. In addition, the MRI controller 146 may be combined with the transducer controller 108 into an integrated system control facility. In addition, the ultrasound systems 100 may be displaced within the bore 106 and integrated with the MRI apparatus 132.

Figure 2A:
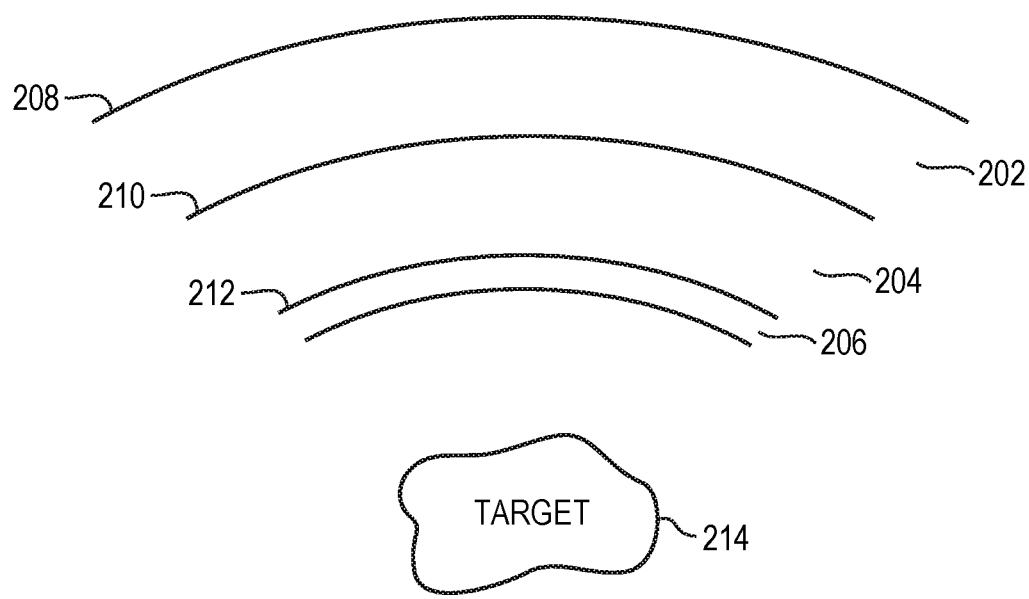
FIG. 2A schematically illustrates tissue layers of a human skull.

Referring to FIG. 2A, a typical human skull 114 has multiple tissue layers, including an external layer 202, a bone marrow layer 204, and an internal layer or cortex 206; each layer of the skull 114 may be highly irregular in shape, thickness and density, and unique to a patient. As a result, when the ultrasound waves emitted from the system 100 encounter the skull 114, part of the incident acoustic energy may be reflected at the interfaces 208, 210, 212; the remaining energy may be partially absorbed, and partially refracted and propagated through the skull 114 depending on the frequency of the waves and the material characteristics and structural inhomogeneity of the skull 114. Because the frequency of the ultrasound waves is controllable, the effects of wave propagation through the skull 114 and the generated focal zone of the waves may be estimated in accordance with the structural inhomogeneity of the skull 114 as further described below.

Figure 2B:
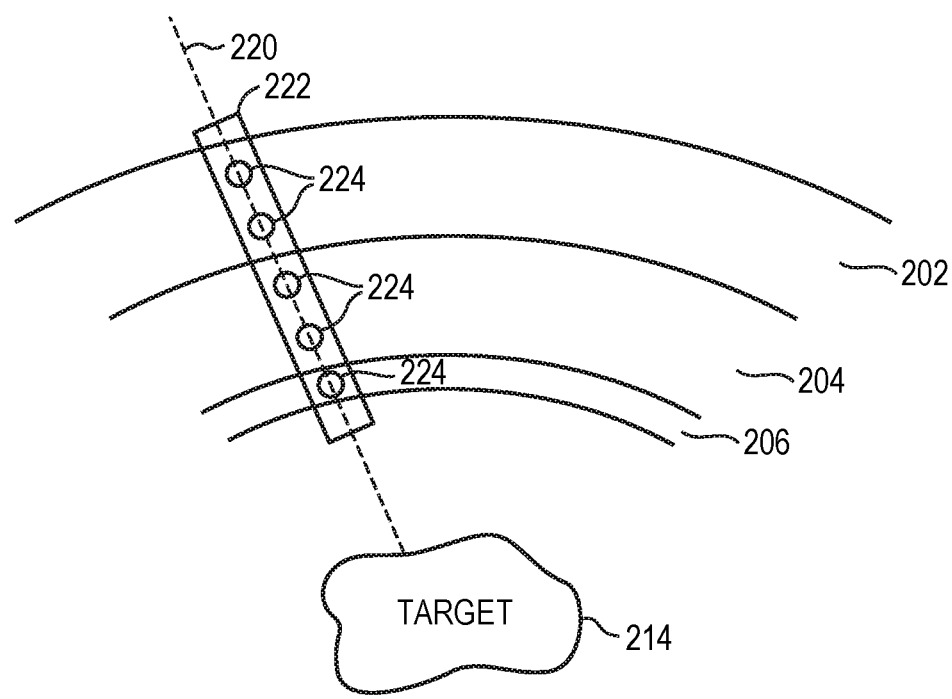
FIG. 2B schematically illustrates image analysis used to determine anatomical characteristics of a patient's skull in accordance with various embodiments of the present invention.

In various embodiments, the structural inhomogeneity of the skull 114 is characterized using an indicator determined based on images acquired using the imager 112. For example, the indicator may be a quantified skull density obtained from CT images. FIG. 2B illustrates an acoustic ray 220 traveling through a CT volume 222 representing a skull region to the target region 214 in the brain. In some embodiments, pixel values 224 (typically measured in "Hounsfield units," "CT values," or "CT numbers") along the path of the ray 220 and spanning the distance between the target region 214 and each transducer element 104 are determined and arranged to form a CT intensity profile for each skull region 222. In various embodiments, the acquired pixel values 224 along the path of the acoustic ray 220 are averaged; the average CT value thus represents an average skull density along the path of the acoustic ray 220 for the skull region 222.

Figure 2C:
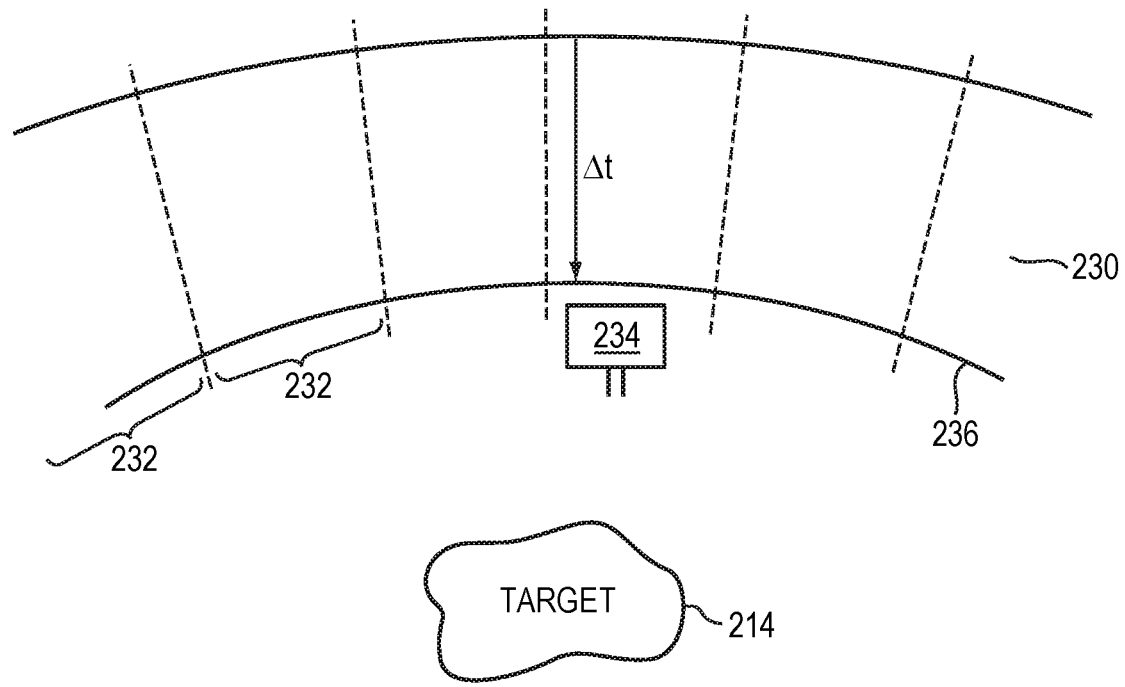
FIG. 2C illustrates an approach for measuring a speed of ultrasound waves in a skull region in accordance with various embodiments of the present invention.

In various embodiments, an acoustic ray model is implemented to compute a speed of ultrasound waves, $C_S$, in the skull region, and thereby determine a beam path of ultrasound waves penetrating therein. Referring to FIG. 2C, the acoustic ray model may simulate the skull 114 as a single layer 230 defined by multiple regions 232; each region is characterized by its material properties (e.g., an average skull density) represented by an average of the CT values measured in the region as described above. To determine the speed of ultrasound waves traversing each skull region 232, a relationship between the average CT value of each region 232 and the speed of ultrasound waves, $C_S$, may be first empirically established from a pre-clinical study, a pre-treatment procedure, and/or from known literature. For example, in a pre-clinical study, a sensor 234 may be placed at an inner surface 236 of the modeled single-layer skull 230 for measuring a travel time, $\Delta t$, of an ultrasound pulse penetrating a skull region 232. The speed of ultrasound waves in the skull region 232 may be computed based on the detected ultrasound travel time and the thickness of the skull region 232 acquired from, for example, the CT images. The sensor 234 may be placed along the entire inner skull surface 236 and detecting the travel time associated with each skull region 232; based thereon, the speed of ultrasound waves transmitting various skull regions 232 can be computed. Because the speed of sound in a material typically correlates to the density thereof, and the density of each skull region 232 may be characterized using the average of CT values measured in each region 232, a relationship between the average of CT values in a skull region and the speed of ultrasound waves therein may be established.

For example, the relationship between the averages of CT values and speeds of ultrasound waves in the skull regions may be a polynomial equation—e.g., the speed of ultrasound waves is a polynomial function of the measured CT values. For example, referring to FIG. 2D, the relationship can be as simple as a linear polynomial obtained using a regression approach:

$$C_S = a + b \times \rho_{CT}$$

where $C_S$ and $\rho_{CT}$ represent the speed of ultrasound waves and averaged CT value associated with the skull region, respectively, and a and b are coefficients determined using the regression approach. Accordingly, when an averaged CT value associated with a specific skull region 232 is acquired from the CT images, the speed of ultrasound waves, $C_S$, traversing this specific skull region can be determined based on the polynomial equation. Generally, the computed speed of ultrasound waves in the skull is in a range between 2,000 m/s and 3,000 m/s.

While an average of the CT values measured in a skull region is utilized herein to represent the average skull density, other indicator may be used to characterize the structural inhomogeneity of the skull. For example, the indicator may include a skull density ratio as described in U.S. Patent Publication No. 2016/0184026, the entire disclosure of which is hereby incorporated by reference.

In addition, the density of brain tissue and the speed of ultrasound waves, $C_B$, in brain tissue may be measured and/or estimated in accordance with the approach described above for the skull tissue. A different brain region may have the same or different speed of ultrasound waves therein, depending on the density of the brain region. A relationship between the density of brain tissue and the speed of ultrasound waves in brain tissue may also be determined based on the approach described above. Alternatively, information about the brain tissue may be acquired from known literature. For example, the speed of sound in brain tissue, $C_B$, has been reported to be approximately 1,545 m/s. In one implementation, the acoustic ray model simulates the brain tissue as a homogeneous soft material and the speed of ultrasound waves therein has the same value, 1,545 m/s, across the entire region. The acoustic ray model may then predict the ultrasound beam path in the skull and brain tissue based on the speeds of ultrasound waves therein as further described below.

Figure 3A:
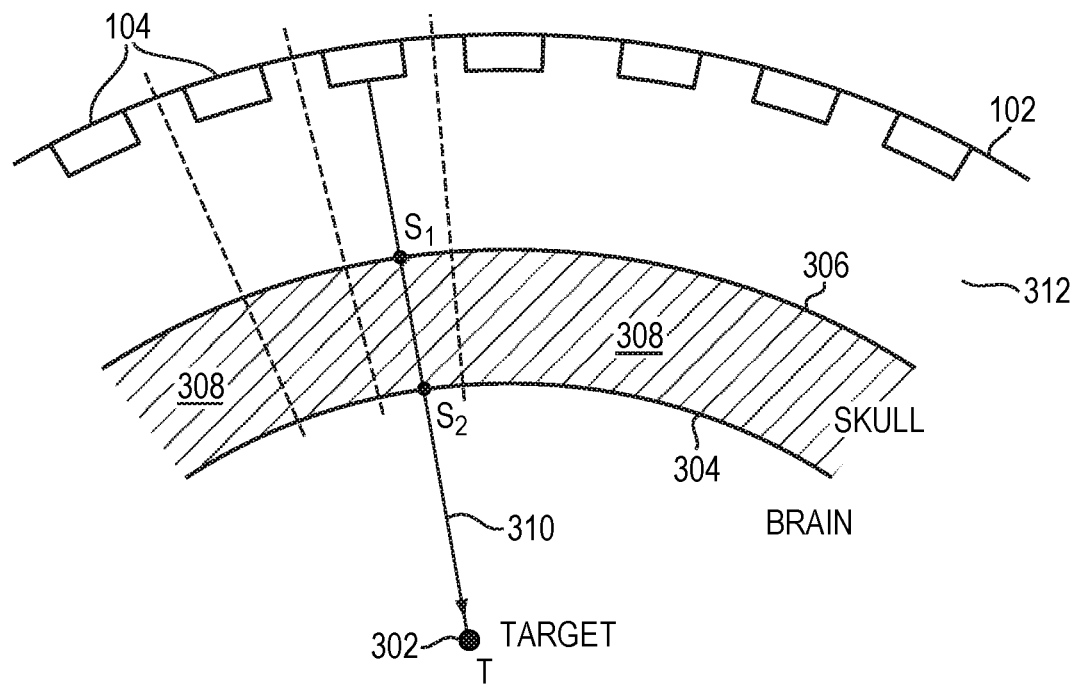
FIG. 3A depicts an initial beam path prediction of ultrasound waves traversing a skull region in accordance with various embodiments of the present invention.

Referring to FIG. 3A, prior to estimating the ultrasound beam path in the skull and brain tissue, the acoustic ray model may first identify the location of the target region 302 (e.g., a tumor in the brain) using, for example, MRI image data. In addition, the acoustic ray model may define boundaries 304, 306 of the skull by, for example, fitting planes to skull edges illustrated in CT image data. In various embodiments, the MRI image data of the skull, brain, and/or transducer elements is utilized to register the CT image data, transducer geometry and/or anatomical characteristics of the skull and brain. Exemplary registration approaches for images acquired using various modalities are provided, for example, in U.S. patent application Ser. Nos. 14/879,235 and 15/155,171, the entire disclosures of which are hereby incorporated by reference. In addition, the acoustic ray model may define the skull as multiple regions 308, where each of the skull regions 308 is related to or corresponds to a particular transducer element 104 or a grouping of elements. Based on the application, the transducer elements 104 may be exposed in air or mounted within a casing filled with a medium (e.g., water).

Figure 2D:
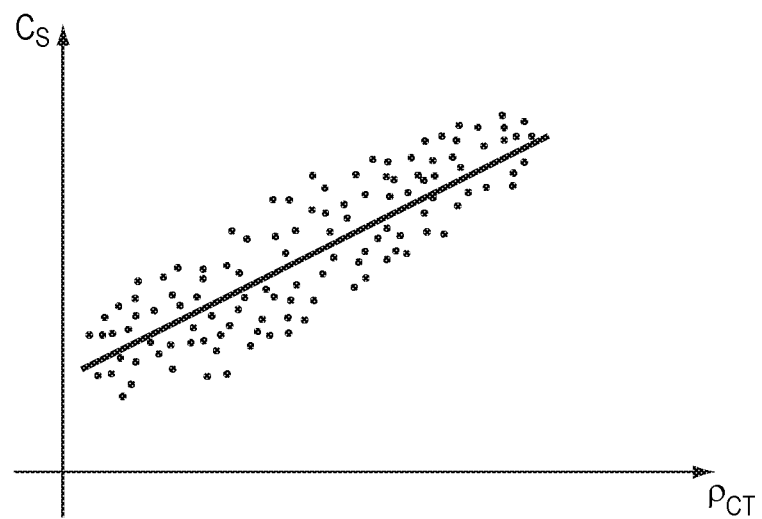
FIG. 2D depicts an exemplary the relationship between CT values obtained in CT imaging data of the skull and the speed of ultrasound waves in the skull.

In various embodiments, the acoustic ray model initially simulates an ultrasound beam path 310 from the transducer element (or group of transducer element) to the target region 302 as a straight line; this initial simulation neglects refraction of the ultrasound waves traversing the skull region. An entry point, $S_1$, of the ultrasound beam 310 into the skull region and an exit point, $S_2$, of the ultrasound beam 310 from the skull region can be identified using the skull boundaries 304, 306 and a straight line extending from the transducer element to the target. In one embodiment, the acoustic ray model acquires CT skull imaging data to extract CT values associated with the skull region located along the beam path 310 between the entry point $S_1$ and exit point $S_2$. By averaging the extracted CT values and utilizing the relationship between the averaged CT values and speeds of ultrasound waves as described above (e.g., a polynomial equation as depicted in FIG. 2D), the speed of ultrasound waves, $C_S$, along the beam path 310 in the skull can be determined.

In addition, the acoustic ray model may acquire a speed of ultrasound waves, $C_M$, in the medium 312 located between the transducer elements 104 and the skull; this information may be obtained either by a sensor measurement as described above using a time-of-flight approach or by lookup from the known literature. Subsequently, the acoustic ray model may determine the beam path of ultrasound waves in the skull region 308 based on the speeds of ultrasound waves, $C_M$ and $C_S$, in the medium and skull region, respectively.

Figure 3B:
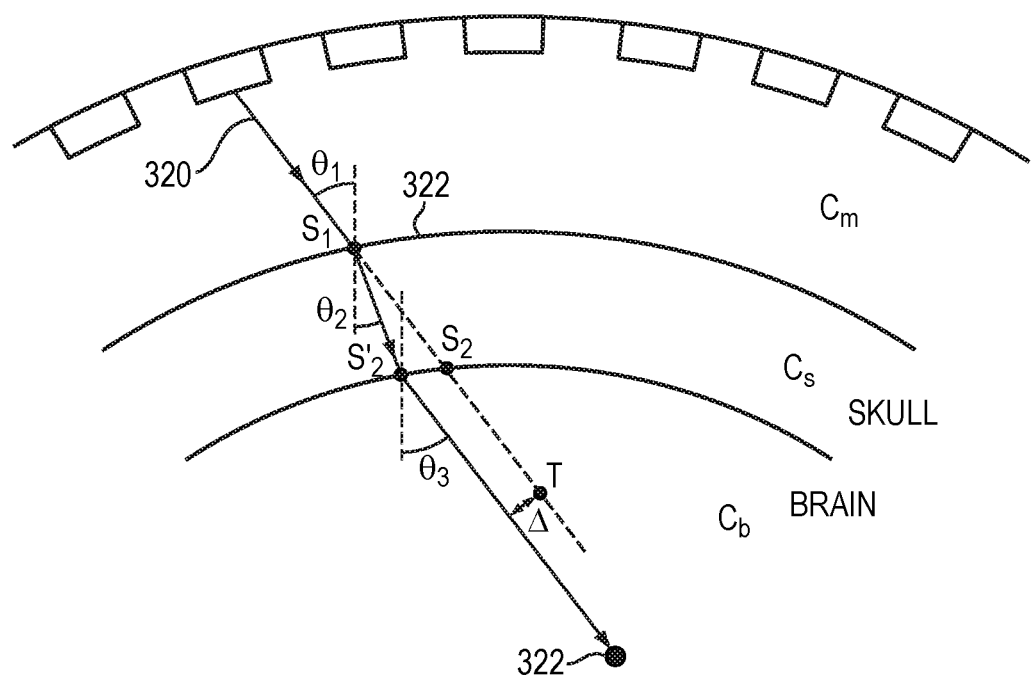
FIG. 3B depicts a prediction of an ultrasound beam path in a skull region by accounting for refraction therein in accordance with various embodiments of the present invention.

In one embodiment, the acoustic ray model utilizes Snell's law to predict the beam path of ultrasound waves traversing the skull region towards the target. For example, referring to FIG. 3B, the angle of incidence, $\theta_1$, of the ultrasound wave 320 transmitted from a transducer element 104 (or a grouping of elements) onto a skull region 322 can be computed based on information about the geometry of the transducer element 104 and the transducer element location and orientation relative to the skull regions 322 as well as the location of the target region 302. The angle of refraction, $\theta_2$, of the ultrasound wave 310 at the entry point $S_1$ of the skull may be computed using Snell's law:

$$\frac{\sin(\theta_1)}{\sin(\theta_2)} = \frac{c_M}{c_S}$$

where $c_M$ and $c_S$ are speeds of ultrasound waves in the medium and skull, respectively. Similarly, an angle of refraction, $\theta_3$, of the ultrasound wave at the exit point $S_2'$ of the skull may be computed as:

$$\frac{\sin(\theta_2)}{\sin(\theta_3)} = \frac{c_S}{c_B}$$

where $c_B$ is the speed of ultrasound waves in the brain tissue. Because the acoustic ray model simulates the skull as a single layer structure, refraction within the skull region may be neglected.

In various embodiments, the acoustic ray model assumes the brain tissue to be homogeneous; accordingly, based on the angle of refraction, $\theta_3$, at the exit point $S_2'$ of the skull, the ultrasound beam path 322 in the brain tissue can be determined. In various embodiments, the acoustic ray model further identifies a point T' on the beam path 322 that has the shortest distance $\Delta$ to the target region T. If the distance $\Delta$ is above a first predetermined threshold, the deviation of the predicted beam path 322 from the target location T is too large to allow a focusing algorithm to efficiently predict a correction phase shift associated with the element S so as to ensure a contribution thereof at the focus in the target region is positive (i.e., in phase with the other elements). In such circumstances, a coarser correction and/or an alternative approach may be required. For example, new images of the target region and/or the skull may be acquired to provide better imaging quality and image analysis may be performed on the new images to more accurately determine the target location and/or characteristics of the skull; the speeds of ultrasound waves in the medium, skull and/or brain tissue may be estimated using another approach; the acoustic ray model may be modified to more accurately predict the ultrasound beam path penetrating the skull to the target region; or the transducer position may be changed.

Figure 3C:
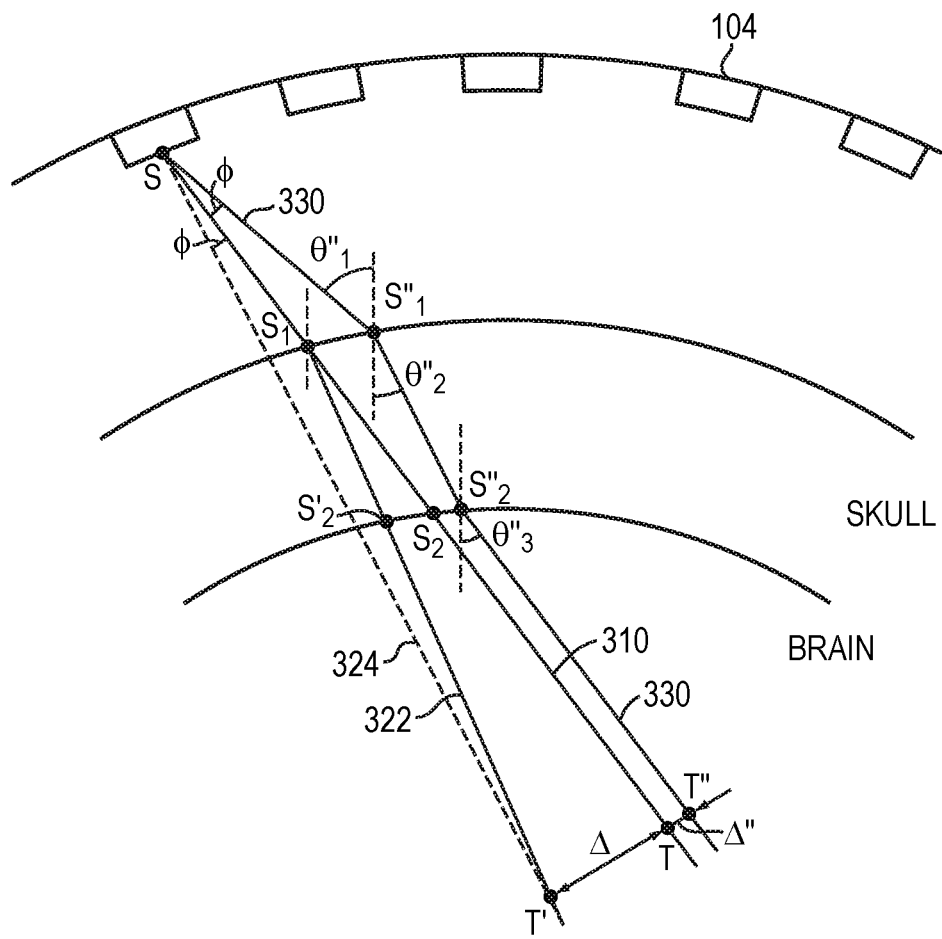
FIGS. 3C and 3D depict prediction of an ultrasound beam path in a skull region utilizing an acoustic path searching procedure in accordance with various embodiments of the present invention.

If the shortest distance between the target region and predicted beam path 322 is below the first predetermined threshold, the deviation is acceptably small and the focusing algorithm may be used to efficiently predict a correction phase shift associated with the element S, thereby ensuring a positive contribution at the focus in the target region. In various embodiments, the deviation $\Delta$ is further compared against a second predetermined threshold—corresponding, for example, to a deviation too small to have a clinically significant effect (e.g., damage to tissue outside a safety margin around the target) or, in other embodiments, too small to be measured; if the deviation is below the second predetermined threshold, it indicates that the deviation of the beam path 322 from the target location is insignificant. Accordingly, the transducer elements may be activated to create a focal zone along the updated beam path 322 during a focused ultrasound procedure. If, however, the distance $\Delta$ is above the second predetermined threshold, an acoustic-path searching procedure may be performed to eliminate (or at least reduce) the deviation, thereby optimizing the ultrasound phase at the target region. Referring to FIG. 3C, in various embodiments, the acoustic-path searching procedure first determines an angle $\Phi$ between the initial straight-line beam path 310 and a line 324 connecting the transducer element S to the point T' on the predicted beam path 322 that accounts for wave refraction in the skull and brain tissue. Because the deviation $\Delta$ is substantially smaller than the distance from the transducer element to the target region, the angle $\Phi$ (in radians) may be approximated as follows:

$$\Phi = \frac{\Delta}{ST'}$$

Figure 3D:
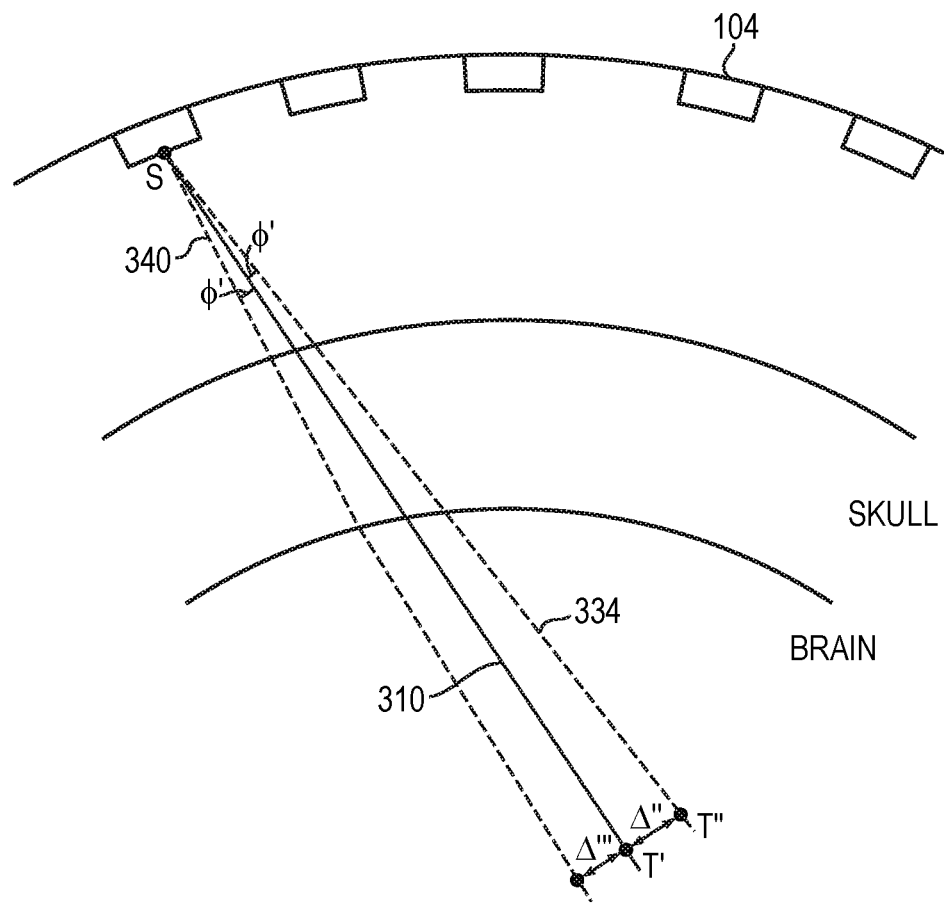

Subsequently, the acoustic ray model updates the estimated ultrasound beam path from the transducer element through the corresponding skull region to the target to be on a beam path 330 that has an angle $\Phi$ with respect to the initial beam path 310. Using the updated beam path 330 from the transducer element, an updated entry point, $S_1''$, and the associated angle of incidence, $\theta_1''$, and angle of refraction, $\theta_2''$, of the ultrasound wave at the updated entry point $S_1''$ can be recomputed. Subsequently, an updated exit point, $S_2''$, and angle of refraction, $\theta_3''$, of the ultrasound wave at the updated exit point $S_2''$ may be determined using Snell's law as described above. The beam path in brain tissue may then be adjusted based on the updated angle of refraction $\theta_3$, and the shortest distance $\Delta''$ from the target region to the updated beam path 330 can be computed. Again, if the shortest distance $\Delta''$ is below the second predetermined threshold, the deviation of the expected beam path 330 from the target location is insignificant; accordingly, the transducer elements may be activated to create a focal zone along the updated beam path 330 during a focused ultrasound procedure. If, however, the distance Δ" is above the second predetermined threshold, the acoustic-path searching procedure may be iteratively performed until the deviation Δ" falls below the second threshold. For example, referring to FIG. 3D, the acoustic-path searching procedure may determine an angle Φ' between the initial straight-line beam path 310 and a line 334 connecting the transducer element S to the point T". Again, because the deviation Δ" is substantially smaller than the distance from the transducer element to the target region, the angle Φ' may be approximated as:

$$\Phi' = \frac{\Delta''}{\overline{ST''}}$$

The acoustic ray model then updates the estimated ultrasound beam path to be on a beam path 340 that has an angle Φ' with respect to the initial beam path 310. Subsequently, an updated deviation Δ'" of the beam path 340 from the target region can be determined.

Although FIGS. 3A-3D depict the patient's skull as a single-layer tissue, the skull may be modeled as a multilayer structure (e.g., three layers). In the multilayer model, the ultrasound ray may be refracted multiple times in the skull region on the way to the target. Again, the beam path may be updated based on the distance between the ray in the brain and the target location. In addition, the initial beam path 310 may be determined using any suitable approach other than the straight-line method as described above. For example, the initial entry point $S_1$ of the ultrasound beam 310 may be identified as a point through which a tangent line to the skull region is perpendicular to the element surface. Subsequently, Snell's law as described may be implemented to predict the beam path of ultrasound waves traversing the skull region towards the target.

Alternatively and/or additionally, in some embodiments, the correction is iteratively performed until the deviation of the beam path from the target region is minimized. For example, assuming the shortest distances between the predicted beam paths and target region are $\Delta_1$, $\Delta_2$, and $\Delta_3$ for the $n^{th}$, $(n+1)^{th}$, and $(n+2)^{th}$ iterations of correction, respectively; if $\Delta_1 > \Delta_2$ and $\Delta_3 > \Delta_2$, the deviation is minimized at the $(n+1)^{th}$ iteration. Accordingly, the phase correction associated with the transducer element may be performed according to the beam path predicted in the $(n+1)^{th}$ iteration. In addition, the iterative acoustic-path searching procedure may be terminated when other conditions are met. For example, the searching procedure may be stopped when too may iterations (e.g., more than 20 times) have been performed or when the improvement of the deviation between two successive iterations is too small (e.g., $\Delta_n - \Delta_{n+1} < 0.1$ mm).

The acoustic ray model may sequentially or simultaneously predict multiple ultrasound beam paths, each associated with waves traversing a different skull region from a corresponding transducer element (or a grouping of corresponding elements). Based on the predicted beam paths and their deviation from the target, the acoustic-path searching procedure may be iteratively performed until the beam paths substantially coincide with the target region. To ensure the focus of the ultrasound waves is at the target region, the focus algorithm may determine the phase shift associated with each transducer element such that the ultrasound beams traversing the multiple skull regions collectively form a constructive focal zone at the target region. In one embodiment, the phase shift associated with each transducer element is determined based on the path between the transducer element and the target location and/or and/or the speed of ultrasound waves in each region along the path. In addition, the phases of ultrasound beams whose paths are not found and/or not considered optimal (e.g., not substantially coinciding with the target region) may not be synchronized between the transmitting transducer elements. Therefore, these beams may be out of phase and destructively interfere to avoid damage to healthy tissue surrounding the target region. If one or more undesired hot spots are generated, various approaches may be implemented to reduce them without substantially reducing the ultrasound intensity at the target region. Exemplary approaches are provided, for example, in U.S. patent application Ser. No. 15/404,412, the entire disclosure of which is hereby incorporated by reference.

Figure 4A:
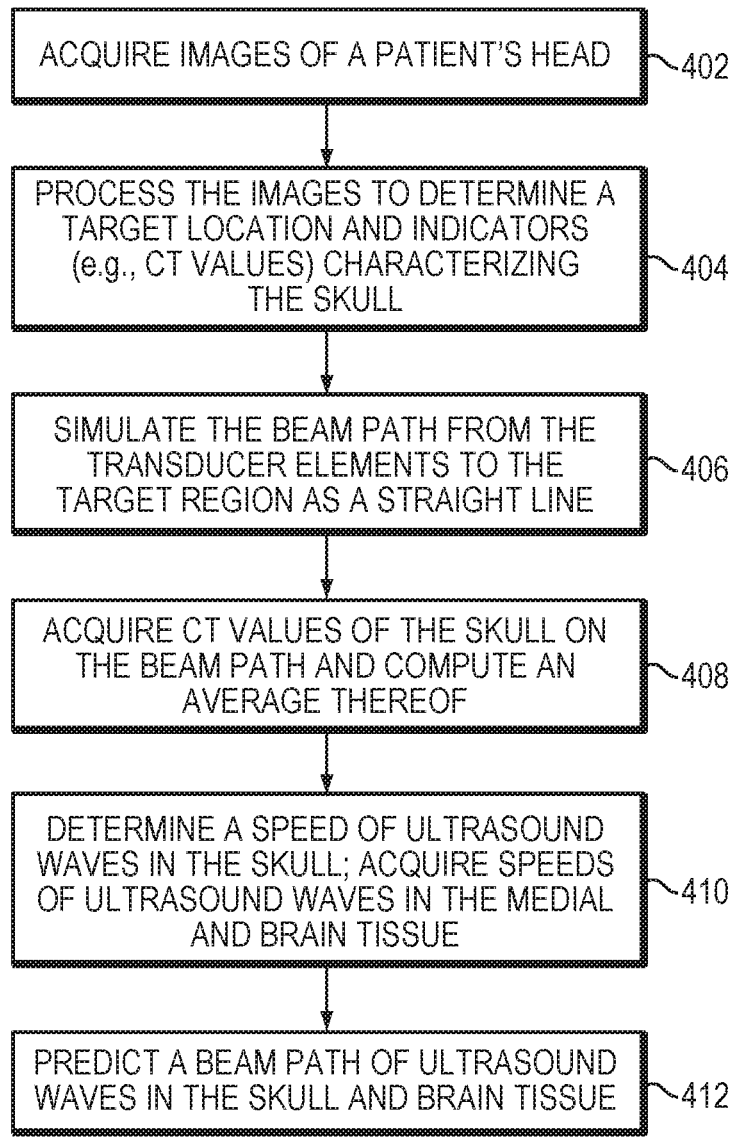
FIG. 4A is a flow chart illustrating an approach for predicting the ultrasound beam path in the skull and brain tissue in accordance with various embodiments of the present invention.

FIG. 4A illustrates an approach for predicting the beam path(s) of ultrasound waves traversing a skull region into the brain tissue in accordance with various embodiments. In a first step 402, images of the patient's head are acquired using an imager; the images may include the skull and/or a target region to be treated. In a second step 404, the images are processed to determine the location of the target as well as indicators (e.g., CT values) characterizing the structural inhomogeneity of the skull and the effects of the inhomogeneities on ultrasound propagation; each indicator may be associated with one region of the skull and the regions collectively cover the anticipated region of the skull through which the ultrasound waves travel prior to reaching the target region. In a third step 406, an acoustic ray model initially simulates the beam path of an ultrasound wave from the transducer elements to the target region as, for example, a straight line. Based on the initial simulation, an entry point of the beam entering the skull and an exit point of the beam exiting the skull are determined. In a fourth step 408, skull CT values along the beam path between the entry and exit points are extracted from the imaging data, and an average of the extracted CT values is computed. In a fifth step 410, the speed of ultrasound waves associated with the averaged CT value in the skull is determined based on the relationship correlating the CT value and the speed of ultrasound waves in the skull established in, for example, a pre-clinical study; such data is readily available or straightforwardly generated without undue experimentation.

Optionally, the speed of ultrasound waves in the brain tissue may be computed using a similar approach. In addition, a medium such as water typically intervenes between the transducer elements and the patient's skin, in which case the speed of ultrasound waves in that medium is computed based on the properties of the medium. In a sixth step 412, the beam paths of ultrasound waves transmitted from the elements to the target region are predicted based on the speeds of ultrasound waves in the medium, skull and brain tissue. The ultrasound beam paths may then be compared with the target location to determine a deviation therebetween.

Figure 4B:
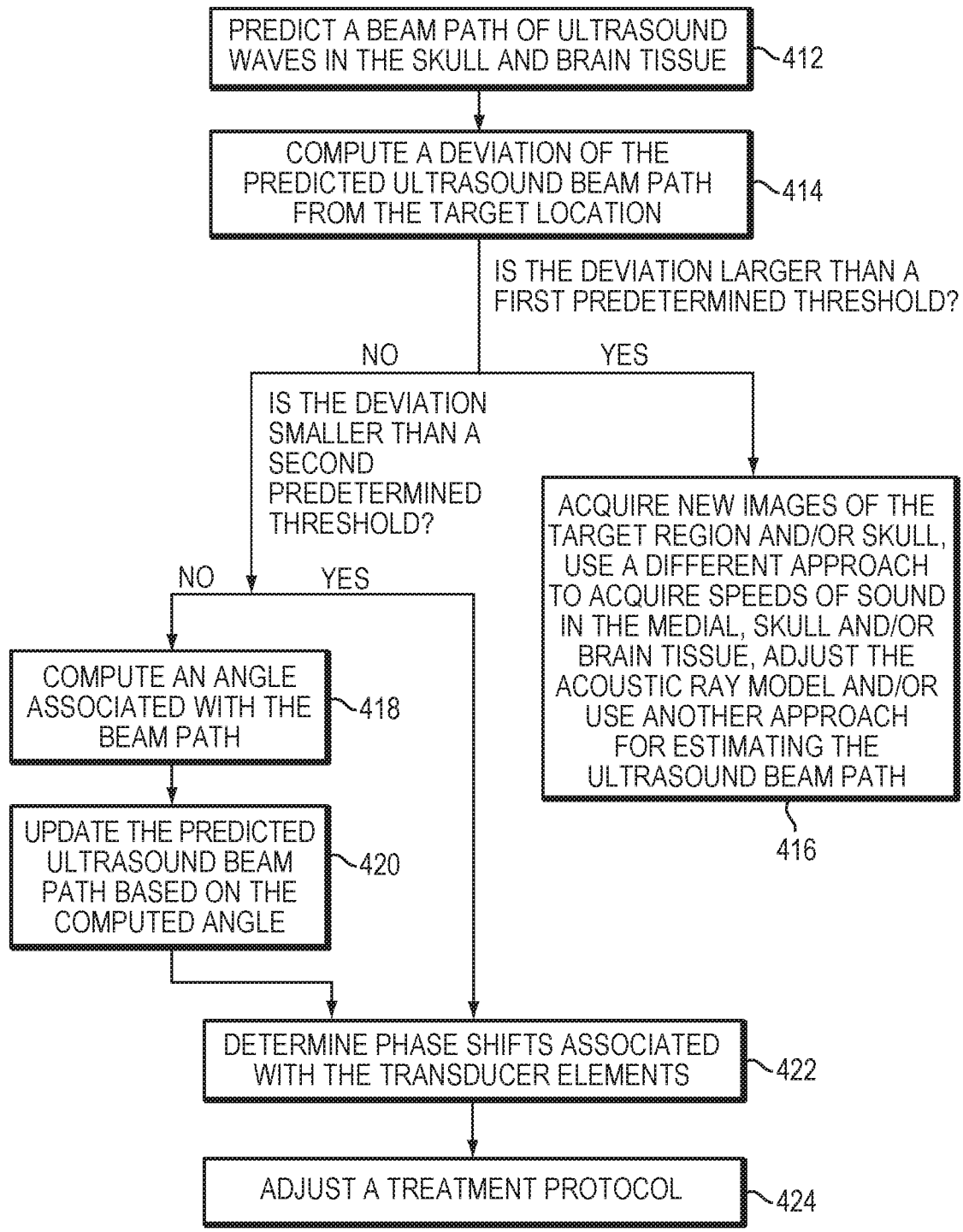
FIG. 4B is a flow chart illustrating a correction approach for minimizing the deviation of the predicted beam path from the target region in accordance with various embodiments.

FIG. 4B illustrates an approach for minimizing the deviation of the predicted beam path from the target region. In various embodiments, after the ultrasound beam path in the skull and brain tissue has been determined as described in step 412, the deviation of the predicted ultrasound beam path from the target region is computed (in a step 414). If the deviation is larger than a first predetermined threshold (as defined above), various approaches, such as acquiring new images of the target region and/or skull, using a different approach to acquire speeds of sound in the medium, skull and/or brain tissue, adjusting the acoustic ray model and/or using another approach for estimating the ultrasound beam path, may be used to generate a new beam path (in a step 416). If the deviation is smaller than the first predetermined threshold but larger than a second predetermined threshold (again as described above), the angle between the initial beam path and a line connecting the transducer element to a point T' on the predicted beam path that accounts for wave refraction in the skull and brain tissue is computed; the point T' is defined as the closest point to the target along the predicted beam path (in a step 418). Subsequently, the acoustic ray model updates the predicted ultrasound beam path to be on a path that has the computed angle relating to the initial beam path (in a step 420). Steps 408-414 may be implemented to determine a new ultrasound beam path traversing the skull region and the deviation between the newly predicted beam path and target region. The deviation between the newly predicted ultrasound beam path and the target region may be computed as described above. Accordingly, steps 408-420 may be iteratively performed until the deviation is below the second predetermined threshold or reaches a minimum. In a step 422, a focusing algorithm may determine phase shifts associated with the transducer elements and the target such that the ultrasound waves traversing the skull collectively form a constructive focal zone at the target region. In a step 424, the transducer elements are activated based on a treatment protocol including, for example, the determined phase shifts and parameters that generate maximal coherency at the target.

Figure 5:
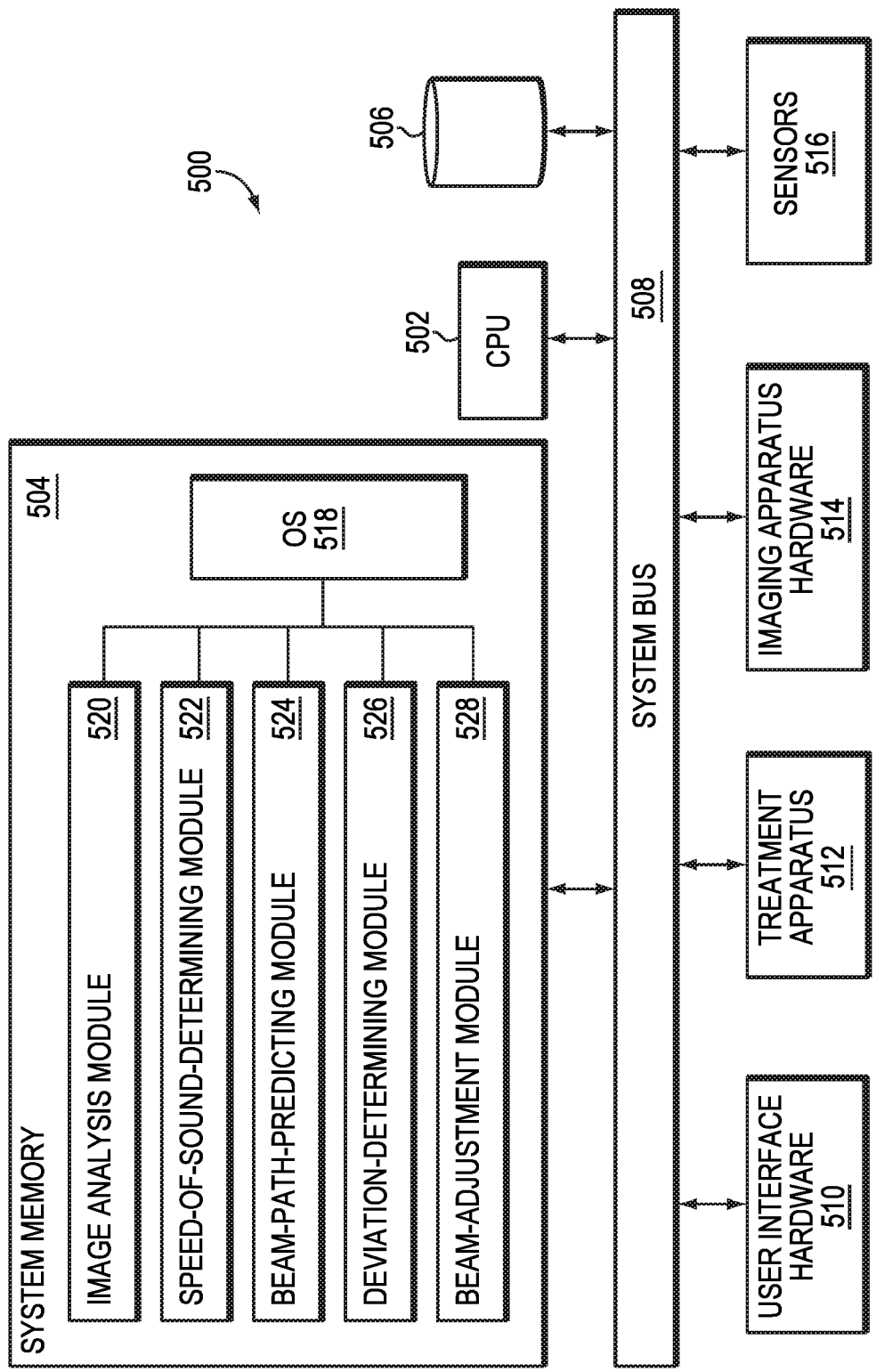
FIG. 5 is a block diagram illustrating an image-processing and control facility in accordance with various embodiments.

Methods for predicting ultrasound beam paths in the skull and brain tissue in accordance herewith can be implemented using a suitable image-processing and control facility (e.g., a controller of the imager, and/or an ultrasound system, or a separate external controller or other computational entity or entities) in communication with the treatment apparatus (e.g., the beam former setting the phases and amplitudes of an ultrasound transducer array and/or the motor or manipulator setting the orientations of the transducer array) 100 and the imaging apparatus 112. The image-processing and control facility may be implemented in any suitable combination of hardware, software, firmware, or hardwiring. FIG. 5 illustrates an exemplary embodiment where the facility is provided by a suitably programmed general-purpose computer 500. The computer includes a central processing unit (CPU) 502, system memory 504, and non-volatile mass storage devices 506 (such as, e.g., one or more hard disks and/or optical storage units). The computer 500 further includes a bidirectional system bus 508 over which the CPU 502, memory 504, and storage devices 506 communicate with each other and with internal or external input/output devices, such as traditional user interface components 510 (including, e.g., a screen, a keyboard, and a mouse) as well as the treatment apparatus 512, the imaging apparatus 514, and (optionally) any sensors 516 measuring the travel time of ultrasound waves through various skull and/or brain regions.

The system memory 504 contains instructions, conceptually illustrated as a group of modules, that control the operation of CPU 502 and its interaction with the other hardware components. An operating system 518 directs the execution of low-level, basic system functions such as memory allocation, file management and operation of mass storage devices 506. At a high level, one or more service applications provide the computational functionality required for image-processing and ultrasound beam path prediction. For example, as illustrated, the system may include a conventional image-analysis module 520 for acquiring image data received from the imaging apparatus 514, and based thereon identifying a location of the target region, determining the distance between the target region (e.g., its center of mass) and at least a portion of the treatment apparatus 512, and/or extracting an indicator characterizing tissue inhomogeneity; a speed-of-sound-determining module 522 for determining the speed of ultrasound waves traversing various regions of the skull and/or brain tissue based on an empirical pre-clinical study, a sensor measurement performed in a pre-treatment procedure, and/or reports obtained from known literature; a beam-path-predicting module 524 for predicting the ultrasound waves in the skull and/or brain tissue in accordance with the techniques described above; and a deviation-determining module 526 for computing, in the manner set forth above, a deviation from the prediction beam path to the target location and comparing the computed deviation with predetermined thresholds.

In addition, the system may include a beam-adjustment module 528 for computing amplitudes, phase shifts and/or other parameters of the treatment apparatus to account for refraction in the skull and/or brain tissue so as to generate a focus at the target location. For example, the beam-adjustment module 528 may be responsive to the deviation-determining module 526 and, based on the determined deviation, may thereby compute correction of ultrasound parameter(s) necessary to reduce or eliminate the deviation. The correction may then be transmitted to the transducer-adjustment mechanism 117, which acts mechanically or via beamformer 106. The mode of action may depend on the magnitude of the required adjustment (e.g., mechanical for coarse adjustment and electronic for fine adjustment) and/or the configuration selected for the transducer-adjustment mechanism. In addition, the phase shifts may be determined based on the path between the treatment apparatus and the target location identified by the image-analysis module 520. The computed parameters may then be communicated to the ultrasound controller for activating the transducer array. The various modules may be programmed in any suitable programming language, including, without limitation, high-level languages such as C, C++, C #, Ada, Basic, Cobra, Fortran, Java, Lisp, Perl, Python, Ruby, or Object Pascal, or low-level assembly languages; in some embodiments, different modules are programmed in different languages.

In addition, the term "controller" used herein broadly includes all necessary hardware components and/or software modules utilized to perform any functionality as described above; the controller may include multiple hardware components and/or software modules and the functionality can be spread among different components and/or modules.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A method of transmitting ultrasound waves from at least one transducer element and traversing a patient's skull into a target region utilizing data of the patient's skull, the method comprising:
   (a) predicting a first beam path of the ultrasound waves traversing the skull into the target region based at least in part on a location of the target region;
   (b) computationally determining structural characteristics of the skull along the first beam path based on the skull data;
   (c) predicting a second beam path of the ultrasound waves traversing the skull based at least in part on the determined structural characteristics;
   (d) updating the second beam path of the ultrasound waves based at least in part on at least one of a deviation between the second beam path and the location of the target region or the second beam path; and
   (e) activating the at least one transducer element in accordance with a treatment protocol.

2. The method of claim 1, wherein the first beam path is a straight line connecting the at least one transducer element to the target region.

3. The method of claim 1, wherein the skull data is CT imaging data and the structural characteristics are represented by a CT value extracted from the CT imaging data.

4. The method of claim 1, further comprising establishing a relationship between the structural characteristics of a plurality of skull regions and speeds of ultrasound waves traversing the plurality of skull regions.

5. The method of claim 4, further comprising determining a first speed of ultrasound waves traversing the skull.

6. The method of claim 5, wherein the first speed of ultrasound waves is determined based on the relationship and the structural characteristics determined in step (b).

7. The method of claim 5, further comprising determining a second speed of ultrasound waves traversing brain tissue.

8. The method of claim 7, further comprising determining a third speed of ultrasound waves traversing a medium located between the at least one transducer element and the skull.

9. The method of claim 8, wherein the third speed of ultrasound waves is determined based at least in part on a temperature of the medium.

10. The method of claim 8, wherein the second beam path is predicted based at least in part on the first, second and third speeds of ultrasound waves.

11. The method of claim 1, wherein the deviation determination step comprises computing a shortest distance between the second beam path and the location of the target.

12. The method of claim 1, further comprising:
   computing an angle between a first line connecting the at least one transducer element to the location of the target region and a second line connecting the at least one transducer element to a point on the second beam path; and
   updating the second beam path of the ultrasound waves based on the computed angle.

13. The method of claim 12, wherein the point has a shortest distance to the location of the target region on the second beam path.

14. The method of claim 1, wherein the treatment protocol comprises at least one of an amplitude or a phase shift associated with the at least one transducer element.

15. The method of claim 1, wherein the ultrasound waves are transmitted from a plurality of transducer elements and the second beam path of the ultrasound waves is adjusted by altering relative phases of the ultrasound waves emitted from the plurality of transducer elements.

16. The method of claim 1, wherein the ultrasound waves are transmitted from a plurality of transducer elements, the method further comprising computing at least one of amplitudes or phase shifts associated with the plurality of transducer elements so as to generate a focus at the target region.

17. The method of claim 1, wherein the skull comprises a plurality of layers and step (b) comprises computationally determining structural characteristics of the plurality of layers of the skull based on the skull data, and step (c) comprises predicting the second beam path of the ultrasound waves based at least in part on the determined structural characteristics of the plurality of the skull layers.

18. The method of claim 17, wherein soft tissue located between the at least one element and the skull is modeled as one of the plurality of the skull layers.

19. The method of claim 1, further comprising activating the at least one transducer element based at least in part on the determined second beam path.

20. The method of claim 1, further comprising computationally updating the structural characteristics of the skull based at least in part on the second beam path prior to performing step (d).

21. The method of claim 1, further comprising activating a plurality of transducer elements in accordance with the treatment protocol so as to generate a focus at the target region.

22. The method of claim 1, further comprising, prior to performing step (e):
   (f) computationally determining a second deviation between the updated second beam path and the location of the target region;
   (g) determining whether the second deviation is above a predetermined threshold; and,
   if so, (h) updating the updated second beam path of the ultrasound waves based at least in part on the second deviation,
   wherein steps (f)-(h) are iteratively performed until a stopping condition is satisfied.

23. The method of claim 22, wherein the stopping condition consists of one or more of:
   the second deviation below the predetermined threshold,
   a number of iterations exceeding a predetermined limit, or
   a change in the second deviation between two iterations is below a predetermined minimum.

24. A system for transmitting ultrasound waves traversing a patient's skull into a target region, the system comprising:
   an ultrasound transducer comprising at least one transducer element for transmitting the ultrasound waves; and
   a controller, operably coupled to the ultrasound transducer, configured to:
      (a) acquire data of the patient's skull;
      (b) predict a first beam path of the ultrasound waves traversing the skull into the target region based at least in part on a location of the target region;
      (c) computationally determine structural characteristics of the skull along the first beam path based on the skull data;
      (d) predict a second beam path of the ultrasound waves traversing the skull based at least in part on the determined structural characteristics;
      (e) update the second beam path of the ultrasound waves based at least in part on at least one of a deviation between the second beam path and the location of the target region or the second beam path; and (f) activate the at least one transducer element in accordance with a treatment protocol.

25. The system of claim 24, wherein the controller is configured to predict the first beam path using a straight line connecting the at least one transducer element to the target region.

26. The system of claim 24, further comprising an imaging system comprising a computer tomography device for acquiring the skull data, the structural characteristics being represented by a CT value extracted from the imaging data acquired using the computer tomography device.

27. The system of claim 24, wherein the controller is further configured to establish a relationship between the structural characteristics of a plurality of skull regions and speeds of ultrasound waves traversing the plurality of skull regions.

28. The system of claim 27, wherein the controller is further configured to determine a first speed of ultrasound waves traversing the skull.

29. The system of claim 28, wherein the controller is further configured to determine the first speed of ultrasound waves based on the relationship and the structural characteristics determined in step (c).

30. The system of claim 28, wherein the controller is further configured to determine a second speed of ultrasound waves traversing brain tissue inside the skull.

31. The system of claim 30, wherein the controller is further configured to determine a third speed of ultrasound waves traversing a medium located between the at least one transducer element and the skull.

32. The system of claim 31, wherein the controller is further configured to determine the third speed of ultrasound waves based at least in part on a temperature of the medium.

33. The system of claim 31, wherein the controller is further configured to predict the second beam path based at least in part on the first, second and third speeds of ultrasound waves.

34. The system of claim 24, wherein the controller is further configured to compute a shortest distance between the second beam path and the location of the target so as to determine the deviation.

35. The system of claim 24, wherein the controller is further configured to:
compute an angle between a first line connecting the at least one transducer element to the location of the target region and a second line connecting the at least one transducer element to a point on the second beam path; and
update the second beam path of the ultrasound waves based on the computed angle.

36. The system of claim 35, wherein the point has a shortest distance to the location of the target region on the second beam path.

37. The system of claim 24, wherein the treatment protocol comprises at least one of an amplitude or a phase shift associated with the at least one transducer element.

38. The system of claim 24, wherein the ultrasound transducer comprises a plurality of transducer elements and the controller is further configured to update the second beam path of the ultrasound waves by altering relative phases of the ultrasound waves emitted from the plurality of transducer elements.

39. The system of claim 24, wherein the ultrasound transducer comprises a plurality of transducer elements and the controller is further configured to compute at least one of amplitudes or phase shifts associated with the plurality of transducer elements so as to generate a focus at the target region.

40. The system of claim 24, wherein the skull comprises a plurality of layers and the controller is further configured to:
computationally determine structural characteristics of the plurality of layers of the skull based on the skull data in step (c); and
predict the second beam path of the ultrasound waves based at least in part on the determined structural characteristics of the plurality of the skull layers in step (d).

41. The system of claim 40, wherein the controller is further configured to model soft tissue located between the at least one element and the skull as one of the plurality of the skull layers.

42. The system of claim 24, wherein the controller is further configured to activate the at least one transducer element based at least in part on the determined second beam path.

43. The system of claim 24, wherein the controller, prior to performing step (e), is further configured to computationally update the structural characteristics of the skull based at least in part on the second beam path.

44. The system of claim 24, wherein the controller is further configured to activate a plurality of transducer elements in accordance with the treatment protocol so as to generate a focus at the target region.

45. The system of claim 24, wherein the controller, prior to performing step (f), is further configured to:
(g) computationally determine a second deviation between the updated second beam path and the location of the target region;
(h) determine whether the second deviation is above a predetermined threshold; and,
(i) if so, update the updated second beam path of the ultrasound waves based at least in part on the second deviation;
wherein the controller is configured to perform steps (g)-(i) iteratively until a stopping condition is satisfied.

46. The system of claim 45, wherein the stopping condition consists of one or more of:
the second deviation below the predetermined threshold,
a number of iterations exceeding a predetermined limit, or
a change in the second deviation between two iterations is below a predetermined minimum.

* * * * *